US008485999B2

(12) United States Patent
Holmer et al.

(10) Patent No.: US 8,485,999 B2

(45) Date of Patent: Jul. 16, 2013

(54) BLOOD TREATMENT APPARATUS AND METHOD

(75) Inventors: Mattias Holmer, Lund (SE); Lennart Jönsson, Bjärred (SE); Anders Wallenborg, Bjärred (SE); Per Hansson, Åkarp (SE)

(73) Assignee: Gambro Lundia AB, Lund (SE)

( * ) Notice: Subject to any disclaimer, the term of this patent is extended or adjusted under 35 U.S.C. 154(b) by 172 days.

(21) Appl. No.: 13/124,258

(22) PCT Filed: Oct. 12, 2009

(86) PCT No.: PCT/EP2009/063285

§ 371 (c)(1),
(2), (4) Date: Apr. 14, 2011

(87) PCT Pub. No.: WO2010/043593

PCT Pub. Date: Apr. 22, 2010

(65) Prior Publication Data

US 2011/0201988 A1 Aug. 18, 2011

Related U.S. Application Data

(60) Provisional application No. 61/105,052, filed on Oct. 14, 2008.

(30) Foreign Application Priority Data

Oct. 14, 2008 (SE) ...................................... 0802194

(51) Int. Cl.
*A61M 37/00* (2006.01)
*C02F 1/44* (2006.01)

(52) U.S. Cl.
USPC ......... 604/6.11; 604/5.04; 604/6.09; 210/645

(58) Field of Classification Search
USPC ............. 604/4.01, 5.01, 5.04, 6.09, 6.1, 6.11; 210/645, 646.239
See application file for complete search history.

(56) References Cited

U.S. PATENT DOCUMENTS 3,570,672 A 3/1971 Bach
3,881,483 A * 5/1975 Sausse ......................... 604/6.14

(Continued)

FOREIGN PATENT DOCUMENTS

EP 0 516 152 12/1992
EP 0 904 789 3/1999

(Continued)

OTHER PUBLICATIONS

European Search Report and Written Opinion for PCT/EP2009/063285 mailed Dec. 4, 2009.

*Primary Examiner* — Leslie Deak
(74) *Attorney, Agent, or Firm* — Nixon & Vanderhye P.C.

(57) ABSTRACT

A blood treatment apparatus includes: a blood treatment unit, a pair of fluid pumps and a pair of blood pumps. The blood treatment unit is configured to receive untreated blood and fresh blood treatment fluid, and emit treated blood and used blood treatment fluid. The fluid pumps are configured to pass blood treatment fluid through the blood treatment unit. The blood pumps are configured to extract untreated blood from a blood source, pass extracted blood through the blood treatment unit and deliver treated blood to a target vessel. Flow measurement device which determines at least one blood flow parameter reflecting an average flow in relation to the blood treatment unit during a well-defined period of operation of the apparatus, for example while completing one operation cycle. The at least one blood flow parameter is determined based on a difference between (i) a first amount of fresh blood treatment fluid received into the blood treatment unit, and (ii) a second amount of used blood treatment fluid emitted from the blood treatment unit during another well-defined period.

15 Claims, 9 Drawing Sheets

U.S. PATENT DOCUMENTS

Figure 1A:
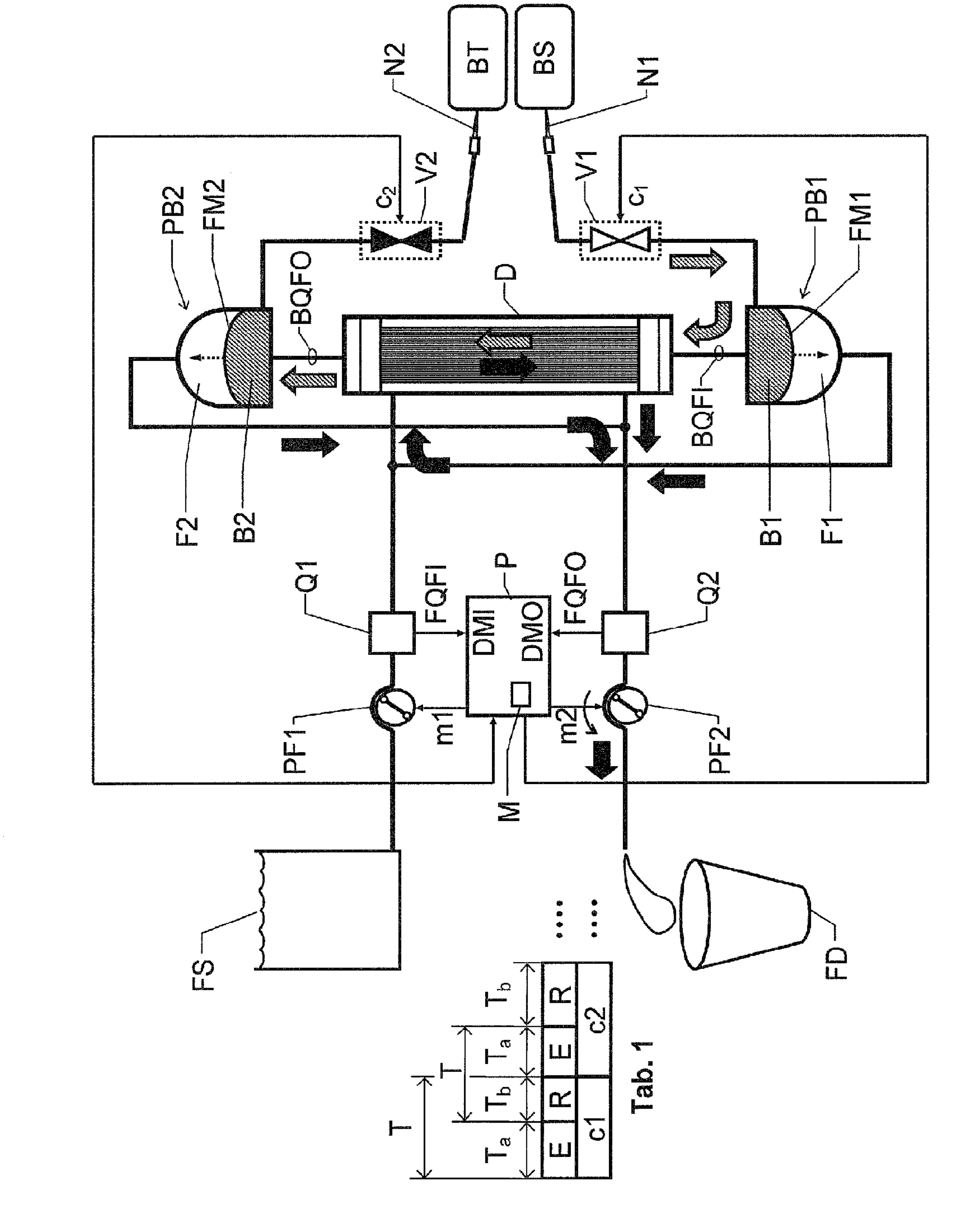

| | | | | | |
|---|---|---|---|---|---|
| 4,490,134 | A | * | 12/1984 | Troutner | 604/6.05 |
| 4,599,165 | A | | 7/1986 | Chevallet | |
| 4,828,543 | A | * | 5/1989 | Weiss et al. | 604/6.09 |
| 5,092,836 | A | * | 3/1992 | Polaschegg | 604/6.11 |
| 5,744,031 | A | | 4/1998 | Bene | |
| 6,110,384 | A | | 8/2000 | Goux et al. | |
| 2005/0230292 | A1 | | 10/2005 | Beden et al. | |
| 2005/0251086 | A1 | | 11/2005 | Sternby | |
| 2010/0042035 | A1 | * | 2/2010 | Moissl et al. | 604/5.04 |

FOREIGN PATENT DOCUMENTS

| | | |
|---|---|---|
| EP | 1 342 479 | 9/2003 |
| WO | 2009/127624 | 10/2009 |

* cited by examiner

BLOOD TREATMENT APPARATUS AND METHOD

CROSS RELATED APPLICATIONS

This application is the US national phase of international application PCT/EP2009/063285 filed 12 Oct. 2009 and claims priority to Swedish Patent Application No. 0802194-1 filed 14 Oct. 2008 and U.S. Provisional Application No. 61/105,052 filed 14 Oct. 2008 which designated the U.S. and the entire contents of each of these applications are hereby incorporated by reference.

THE BACKGROUND OF THE INVENTION AND PRIOR ART

The present invention relates generally to extracorporeal blood treatment. More particularly the invention relates to a blood treatment apparatus according to the preamble of claim 1 and a method according to the preamble of claim 10. The invention likewise pertains to a computer program according to claim 19 and computer readable medium according to claim 20.

A conventional blood treatment apparatus, for instance a hemodialysis system or a hemodiafiltration system, contains a dialysis fluid circuit and a blood circuit. Each circuit is normally associated with at least one pump for transporting the fluid in question. Traditionally, peristaltic pumps have been used, and here the rotational speed of the pump can serve as a basis for determining the flow through the pump, e.g. in the blood circuit. For reasons of patient security and cost efficiency it is further advantageous to avoid including dedicated flow meters in the blood circuit. Hence, in designs including non-peristaltic blood pumps, it may be complicated to measure the blood flow accurately. In fact, also when peristaltic blood pumps are used, the blood flow measure derived from the pump speed may be unreliable. For example if the inlet pressure to the pump becomes negative (or more precisely inlet suction occurs), the rotational speed is a poor fluid flow indicator.

Hence, it is desirable to enable apparatus designs using other types of blood pumps than those operating according to a peristaltic principle. However, there is yet no such solution which renders an accurate blood flow measurement possible, and at the same time avoids the obvious infection/contamination risks associated with a multiple-use flow meter in the blood circuit. Of course, for cost reasons, any single-use flow meters cannot be of high-quality type.

SUMMARY OF THE INVENTION

The object of the present invention is therefore to alleviate the above problems, and provide an accurate, uncomplicated and infection/contamination safe solution for measuring blood flows in relation to a blood treatment unit (i.e. into, out from or both).

According to the invention, the object is achieved by the apparatus as initially described, wherein the flow measurement means is configured to determine the at least one blood flow parameter based on a difference between first and second amounts of blood treatment fluid. The first amount reflects a quantity of fresh blood treatment fluid received into the apparatus comprising the blood treatment unit, the second amount reflects a quantity of used blood treatment fluid emitted from the apparatus, and both amounts are registered during a first well-defined period of operation of the apparatus. The at least one blood flow parameter reflects an average blood flow during a second well-defined period.

The proposed blood treatment apparatus is advantageous because it provides accurate flow measures into as well as out from a blood treatment device while offering high design flexibility in terms of the blood pump characteristics.

According to one embodiment of the invention, it is presumed that the apparatus is configured to operate according to a cyclic process. During a first phase, the untreated blood is extracted from the blood source, and during a second phase, the treated blood is delivered to the target vessel. Here, the first well-defined period represents the time required to complete one of the first and second phases (i.e. either the first or the second phase) at least once, and the second well-defined period represents an interval during which both the first and second phases are completed at least once. Thereby, the flow measurement can be updated repeatedly in a convenient manner.

According to another embodiment of the invention, the fluid pumps are configured to control the operation of the blood pumps via the blood treatment fluid. This is desirable because thereby a compact, cost efficient and comparatively reliable apparatus design is attainable.

According to yet another embodiment of the invention, the apparatus instead includes means for controlling the blood pumps via other means than the blood treatment fluid, such as an incompressible working fluid separated from the blood treatment fluid, or by mechanical means (e.g. in the form of piston pumps). Here, the flow measurement means is configured to determine the flow parameter on the further basis of a respective stroke volume of the blood pumps. This design is advantageous, since it renders it straightforward to determine various process parameters, such as ultrafiltration. Furthermore, piston pumps are desirable, since here, by keeping track of the piston position, it is possible to determine a pumped volume at arbitrary pump positions, i.e. not only at the end positions for the pistons.

According to still another embodiment of the invention, a first parameter of the at least one blood flow parameter reflects a flow of blood into the blood treatment unit. Here, the first well-defined period of operation represents a duration of the first phase, and the second well-defined period represents the duration of the first phase plus the duration of one second phase temporally adjoining the first phase (i.e. a phase of the cyclic process which either follows directly subsequent to the first phase, or a phase immediately preceding the first phase). Thereby, an accurate measure of the blood flow into the blood treatment device can be determined.

According to another embodiment of the invention, as an alternative or a complement to the above-mentioned first parameter, a second parameter of the at least one blood flow parameters reflects a flow of blood out from the blood treatment unit. Here, the first well-defined period of operation instead represents a duration of the second phase of the cyclic process. However, again, the second well-defined period represents the duration of the second phase plus the duration of one first phase temporally adjoining the second phase. Hence, an accurate measure of the blood flow exiting from the blood treatment device can be determined.

According to a further embodiment of the invention, the blood treatment unit includes a semi-permeable membrane structure, e.g. represented by a multitude of hollow fibers whose walls constitute a respective semi-permeable membrane. The blood is being passed on a blood side of said structure, say inside the fibers, and the blood treatment fluid is being passed on a fluid side of said structure, say outside the fibers. Moreover, the apparatus includes means configured to determine an ultrafiltration parameter between the blood and the fluid sides of said structure based on a difference between the first and second amounts of blood treatment fluid. Thus, the blood cleaning process can be controlled more accurately.

According to another aspect of the invention, the object is achieved by the method described initially, the following steps are executed: during a first well-defined period a first amount of fresh blood treatment fluid received into the apparatus comprising the blood treatment unit is registered. A second amount of used blood treatment fluid emitted from the apparatus is also registered during the first well-defined period. Then, after expiry of a second well-defined period, the at least one blood flow parameter is determined as an average blood flow during the second well-defined period. The at least one blood flow parameter is derived based on a difference between the first and second amounts.

According to a further aspect of the invention, the object is achieved by a computer program, which is loadable into the memory of a computer, and includes software adapted to control the method proposed above when said program is run on a computer.

According to another aspect of the invention the object is achieved by a computer readable medium, having a program recorded thereon, where the program is to control a computer to perform the method proposed above when the program is loaded into the computer.

Clearly, the invention is applicable to blood flow measurements in respect of dual-needle implementations. However, the proposed solution is advantageous also for blood treatment apparatuses for executing single-needle hemodialysis or hemodiafiltration, i.e. where the blood source and the target vessel represent the same point of contact with a patient. Further advantages, beneficial features and applications of the present invention will be apparent from the following description and the dependent claims.

BRIEF DESCRIPTION OF THE DRAWINGS AND TABLE

The present invention is now to be explained more closely by means of embodiments, which are disclosed as examples, and with reference to the attached drawings and table.

Figure 1B:
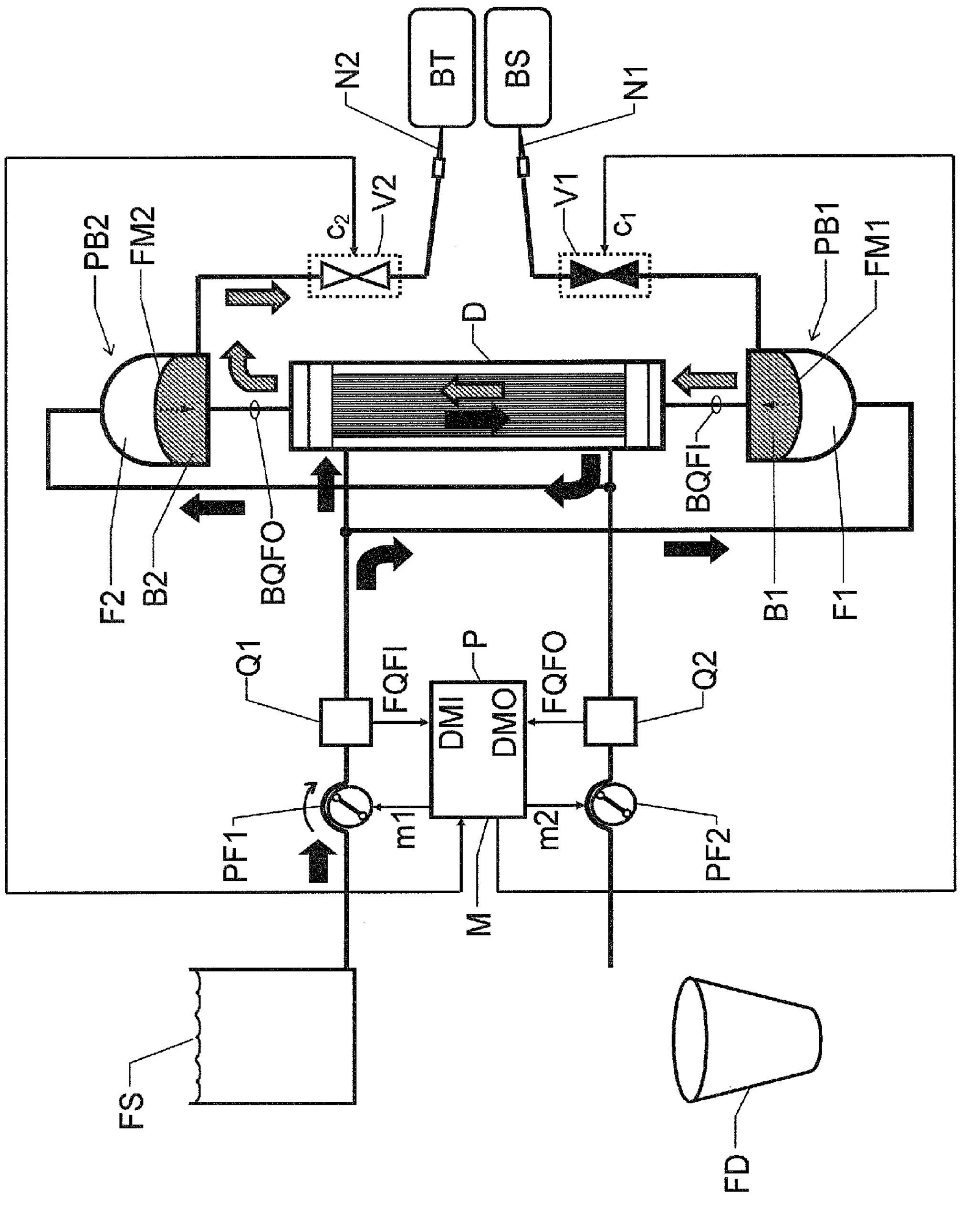
Figure 2A:
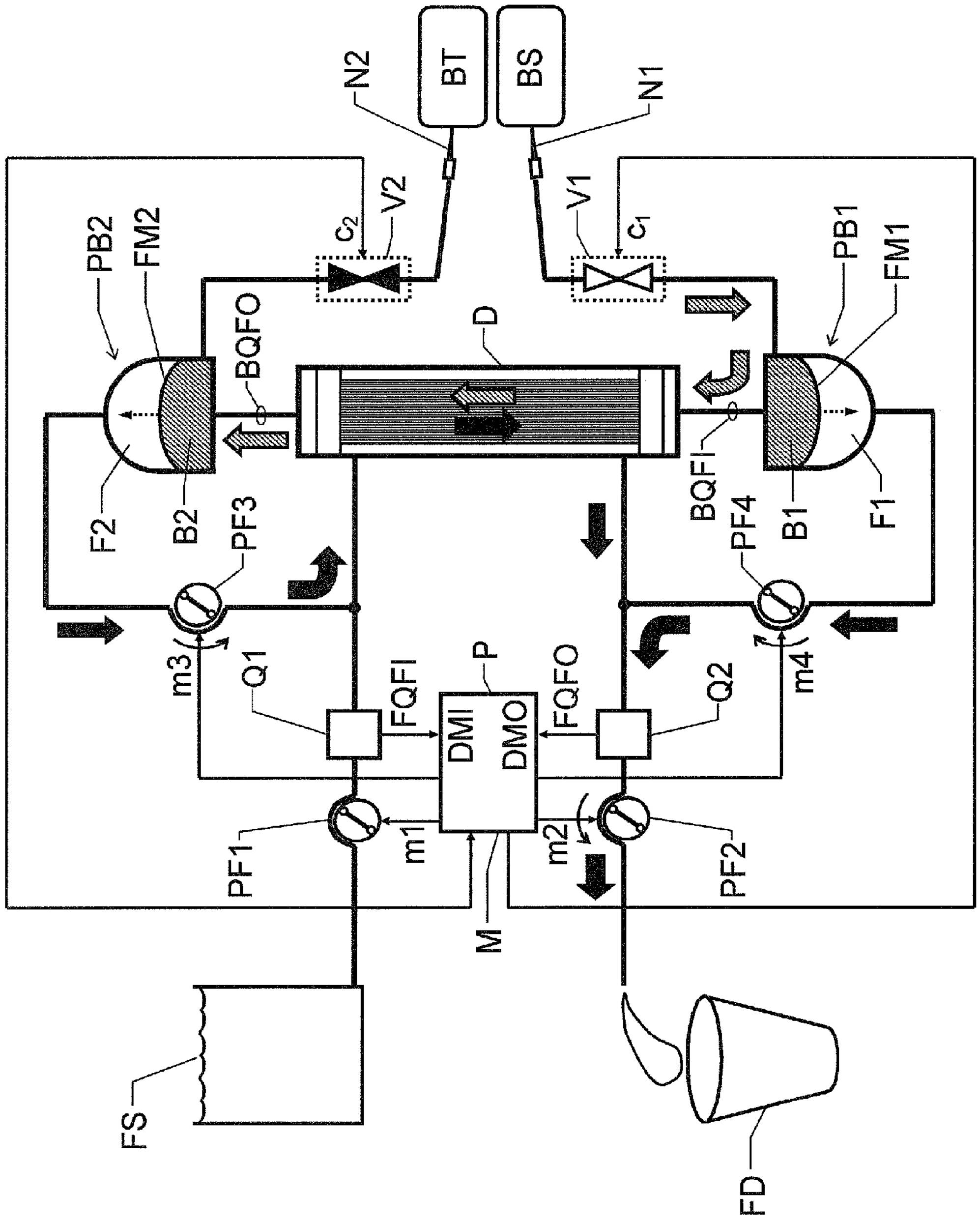
Figure 2B:
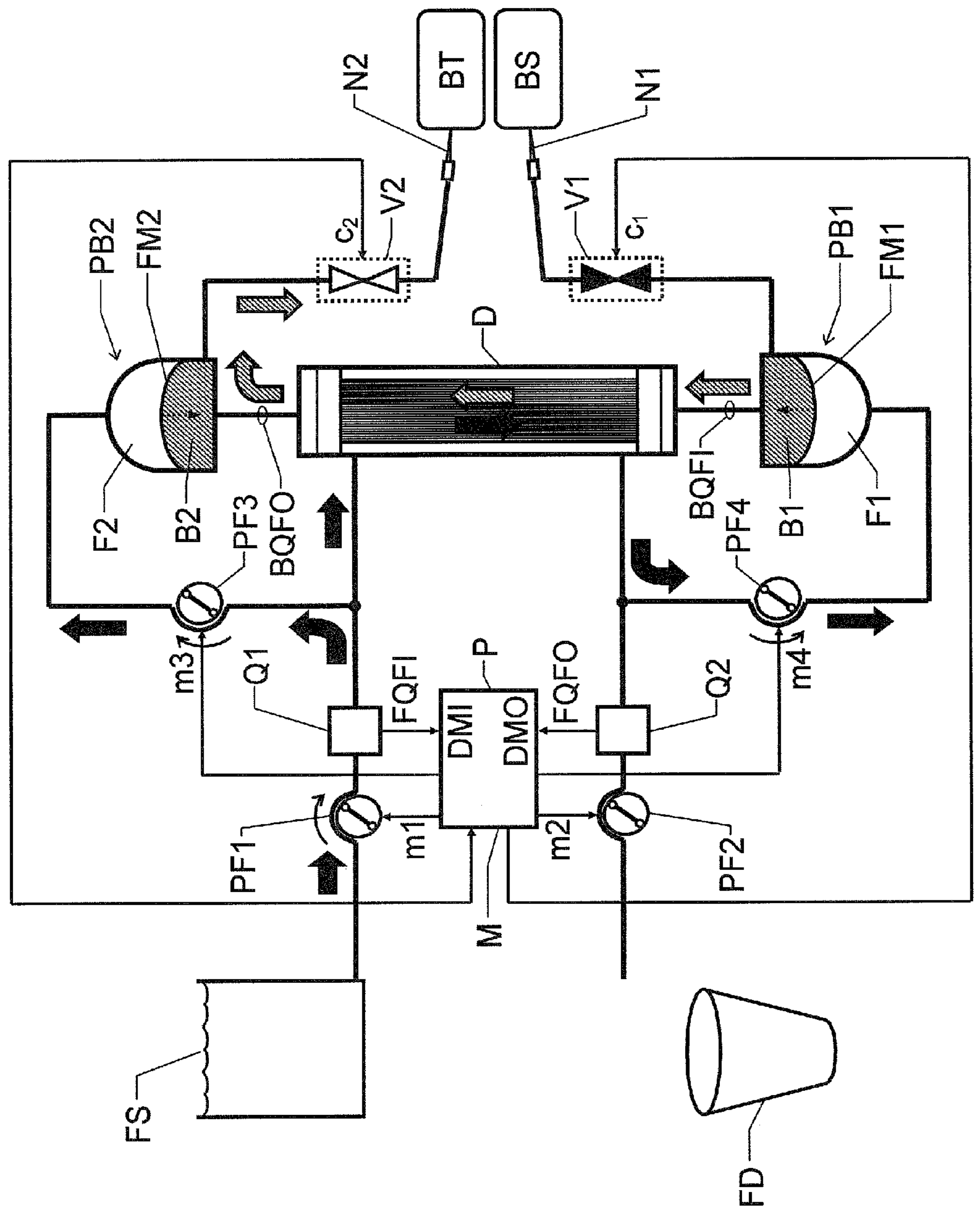
Figure 3A:
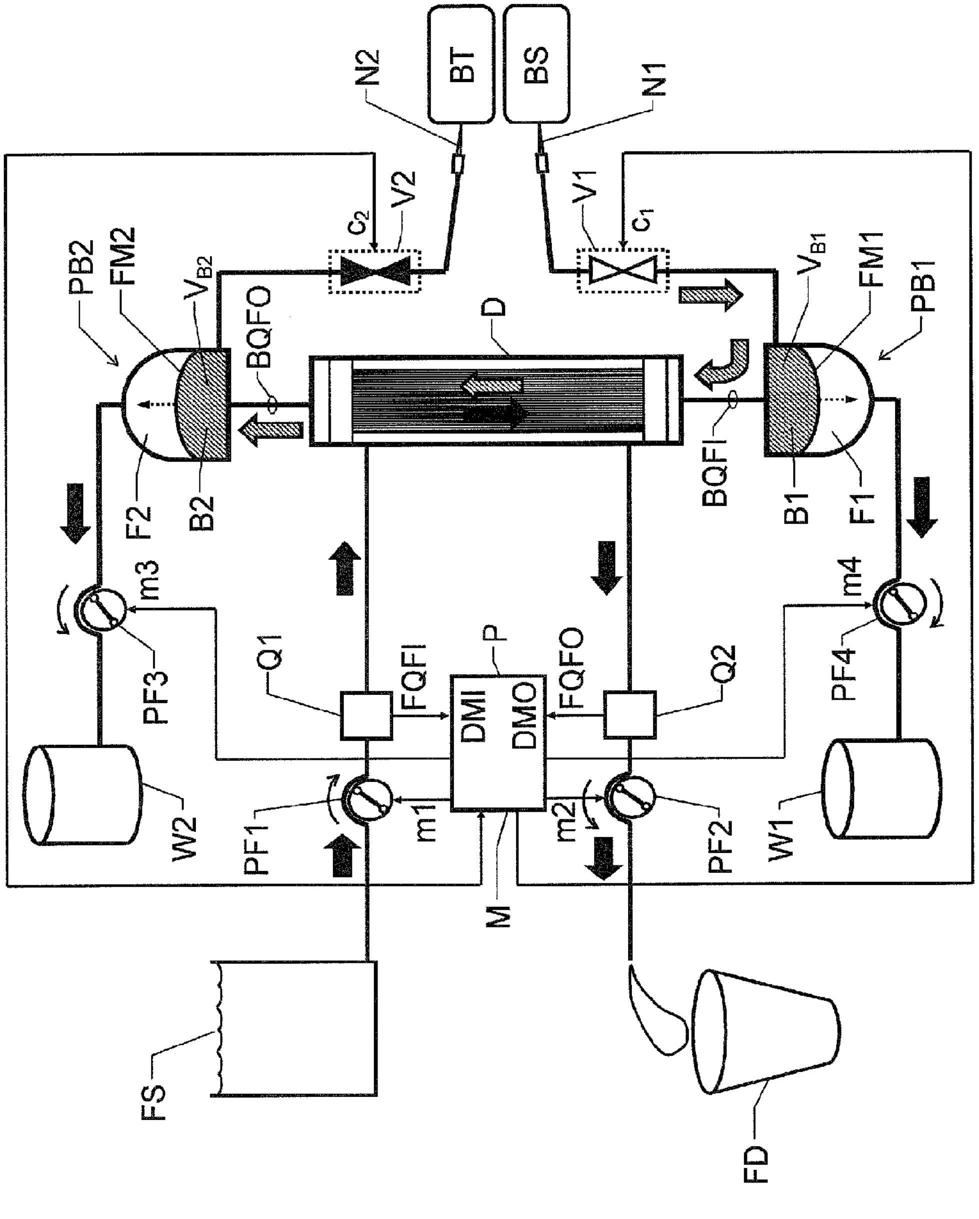
Figure 3B:
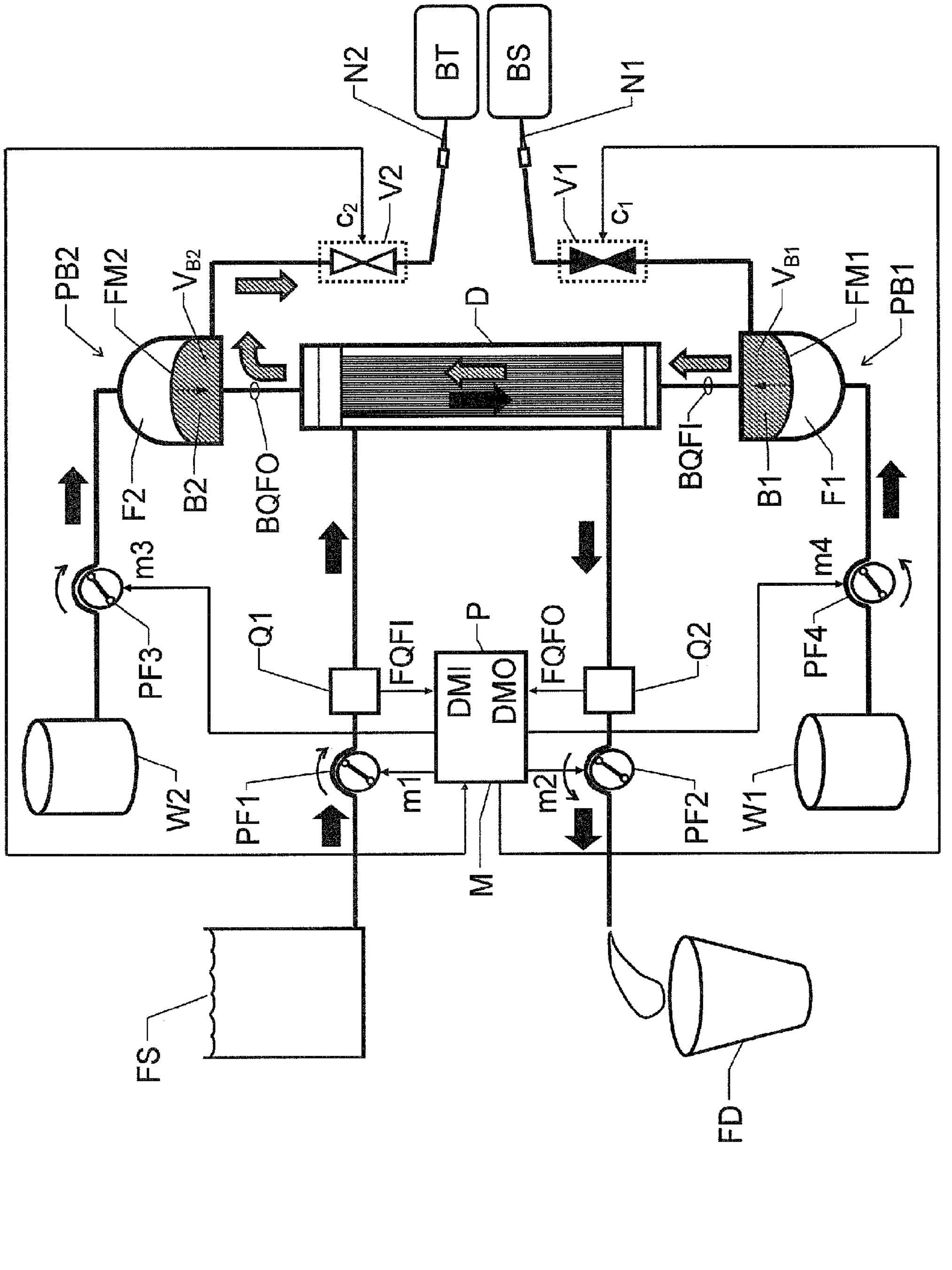
Figure 4A:
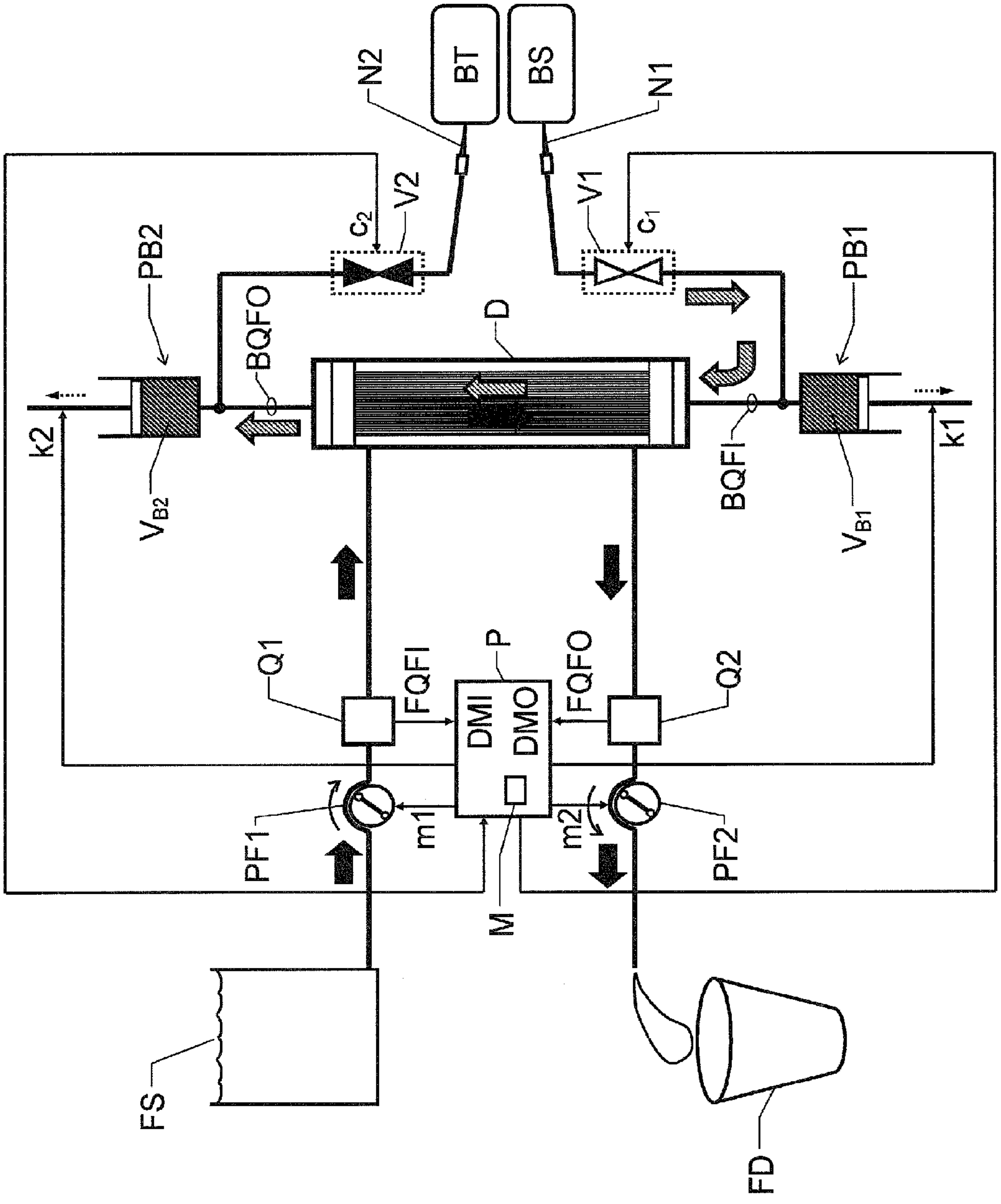
Figure 4B:
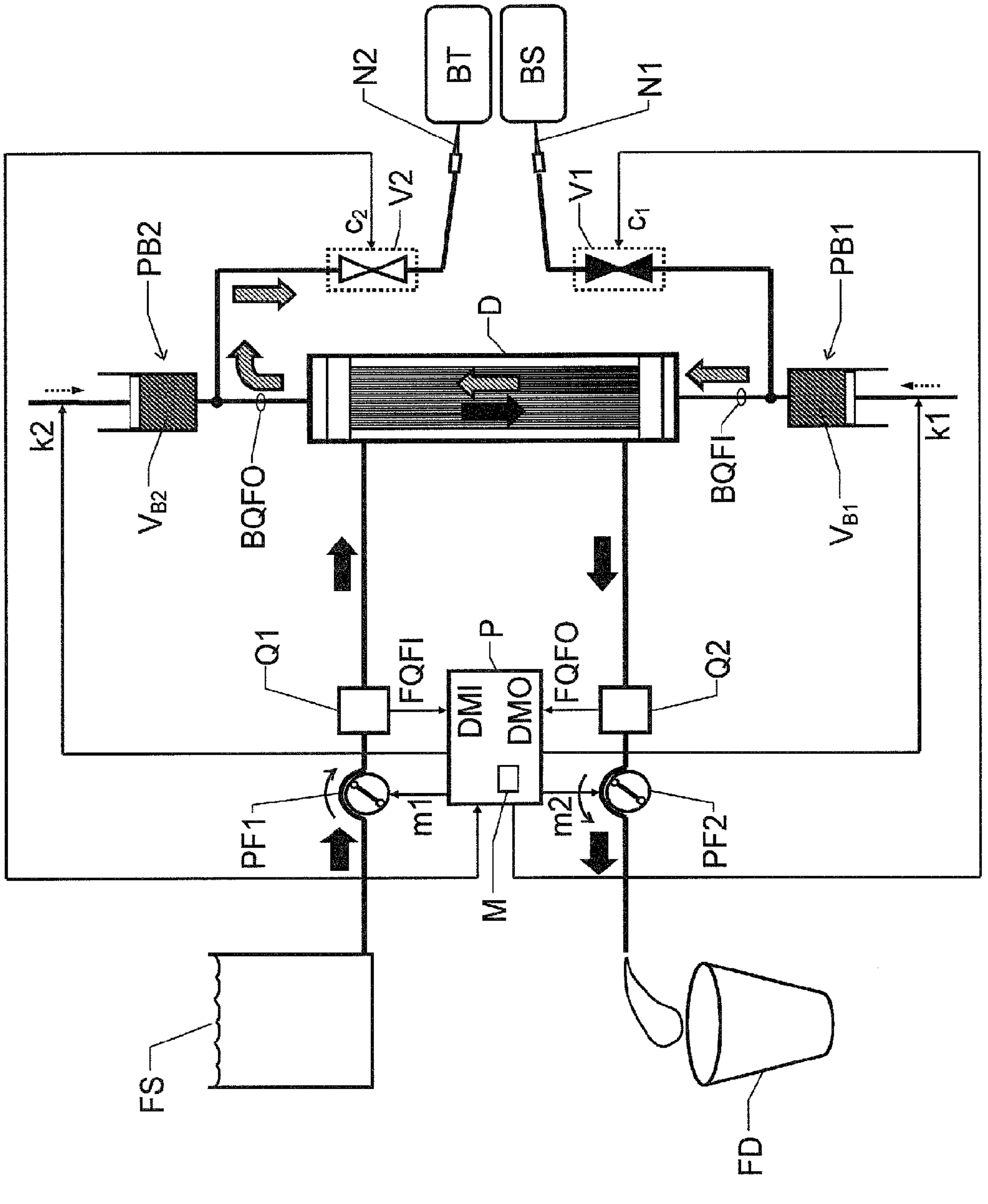
Figure 5:
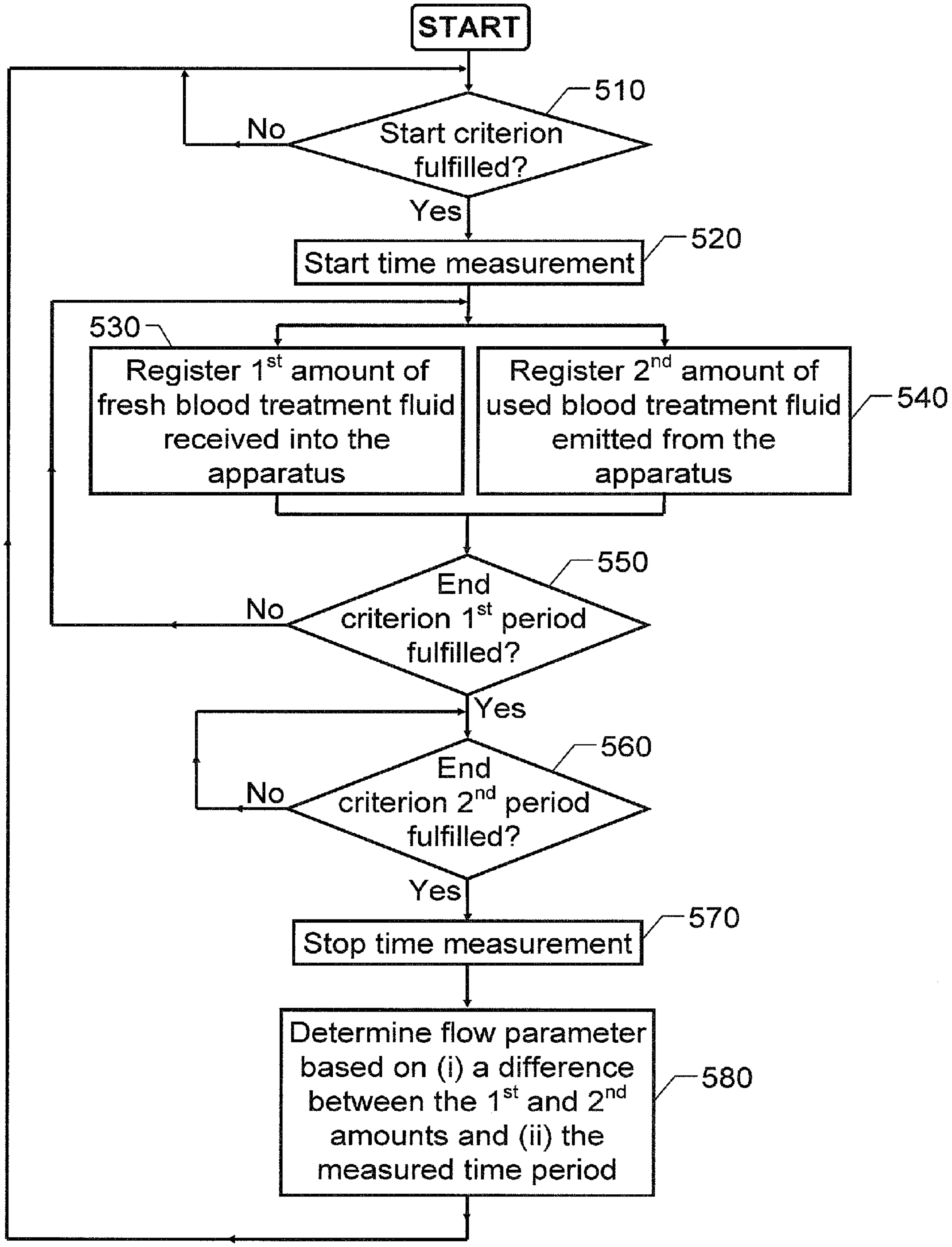

Table 1 shows first and second phases of a proposed cyclic treatment process, first and second well-defined periods during which fluid amounts are registered to determine blood flow values and illustrates the temporal relationships there between;

FIGS. 1*a-b* show block diagrams over a blood treatment apparatus according to a first embodiment of the invention during first and second phases respectively of the cyclic treatment process;

FIGS. 2*a-b* show block diagrams over a blood treatment apparatus according to a second embodiment of the invention during first and second phases respectively of the cyclic treatment process;

FIGS. 3*a-b* show block diagrams over a blood treatment apparatus according to a third embodiment of the invention during first and second phases respectively of the cyclic treatment process;

FIGS. 4*a-b* show block diagrams over a blood treatment apparatus according to a fourth embodiment of the invention during first and second phases respectively of the cyclic treatment process; and FIG. 5 illustrates, by means of a flow diagram, a general method of measuring a blood flow parameter according to the invention.

DESCRIPTION OF EMBODIMENTS OF THE INVENTION

We refer initially to FIG. 1*a*, which shows a block diagram over a blood treatment apparatus (e.g. a dialysis apparatus) according to a first embodiment of the invention during a first phase E of a cyclic blood treatment process.

Table 1 illustrates how the first phase E and a second phase R are related to one another. We assume that a first cycle c1 of the process includes one repetition each of the first and second phases E and R respectively. Then follows a second cycle c2, likewise including one repetition each of the first and second phases E and R, and so on.

The apparatus includes a blood treatment unit D, a pair of fluid pumps PF1 and PF2 respectively, a pair of blood pumps PB1 and PB2 respectively and flow measurement means, which in turn, include first and second flow meters Q1 and Q2 respectively and a control unit P. Moreover, the apparatus includes first and second blood valve means V1 and V2 respectively.

The blood treatment unit D is configured to receive untreated blood from a blood source BS (e.g. represented by a bag containing blood to be treated, or a renal patient), and receive fresh blood treatment fluid originating from a fluid source FS (e.g. a bag of dialysis fluid). The blood treatment unit D is also configured to emit treated blood to a target vessel BT (e.g. represented by a bag for cleaned blood, or a renal patient), and emit used blood treatment fluid (e.g. into the drain, or a waste compartment FD). The blood treatment unit D has a blood side and a fluid side that are separated from one another by means of a semi-permeable membrane structure. For example, this structure may be represented by a large number of hollow fibers whose walls constitute a respective semi-permeable membrane and which fibers are configured to transport blood. The structure is also configured to allow blood treatment fluid to be passed outside said fibers when blood is transported there through. Naturally, the opposite situation is equally well applicable, i.e. that blood treatment fluid is passed through the fibers and blood is passed on the outside thereof. In any case, blood treatment (e.g. dialysis) takes place over each fiber's semi-permeable membrane. Hence, the overall function of the blood treatment unit D is to receive untreated blood and fresh blood treatment fluid, and emit treated blood and used blood treatment fluid.

The fluid pumps PF1 and PF2 are configured to pass blood treatment fluid through the blood treatment unit D. Analogously, the blood pumps PB1 and PB2 are configured to extract untreated blood from the blood source BS, pass extracted blood through the blood treatment unit D and deliver treated blood to the target vessel BT. According to the embodiment of the invention illustrated in FIGS. 1*a* and 1*b*, the fluid pumps PF1 and PF2 are also configured to control the operation of the blood pumps PB1 and PB2 via the blood treatment fluid.

The blood valve means V1 and V2 are controlled to be open and closed in an alternating fashion, such that the first blood valve means V1 is open when the second blood valve means V2 is closed, and vice versa. This results in a cyclic operation of the apparatus, wherein during the first phase E untreated blood is extracted from the blood source BS, and during the second phase R treated blood is delivered to the target vessel BT.

The flow measurement means Q1, Q2 and P are configured to determine at least one blood flow parameter BQFI and/or BQFO, which reflects a flow of blood in relation to the blood treatment unit D. For example a first blood flow parameter BQFI may reflect a flow of blood from the first blood pump PB1 into the blood treatment unit D, and a second blood flow parameter BQFO may reflect a flow of blood out from the blood treatment unit D into the second blood pump PB2. In renal care treatment, these are both critical parameters to monitor. In the following discussion, however, we will focus primarily on the first blood flow parameter BQFI. Namely, after having understood the principles behind how this parameter is determined, it is relatively straightforward to appreciate how the second blood flow parameter BQFO is derived according to embodiments of the invention.

According to one embodiment of the invention, the control unit P is configured to determine the first blood flow parameter BQFI based on a difference between a first amount DMI and a second amount DMO. The first amount DMI represents a quantity of fresh blood treatment fluid received into the apparatus comprising the blood treatment unit D, and the second amount DMO represents a quantity of used blood treatment fluid emitted from the apparatus. The first and second amounts DMI and DMO respectively are registered during a first well-defined period $T_a$ of operation of the apparatus.

Table 1 shows that the first well-defined period $T_a$ is equal to the duration of the first phase E. According to the invention, a second well-defined period T is also defined, which preferably represents an interval during which both of the first and second phases E and R respectively are completed at least once. Hence, another well-defined period $T_b$ may be equal to the duration of the second phase R, such that $T=T_a+T_b$. Consequently, the following relationships are likewise true: $T \geqq T_a$ and $T \geqq T_b$. If the second blood flow parameter BQFO were to be determined, $T_b$ would instead have represented the first well-defined period. It should also be noted that the duration of $T_a$ may be different from the duration of $T_b$, and the cycle duration may vary from cycle to cycle, e.g. between c1 and c2, such that also T varies.

In any case, the first blood flow parameter BQFI represents an average blood flow into the blood treatment unit D during the second well-defined period T. Preferably, the first well-defined period (i.e. $T_a$ or $T_b$) represents the time required to complete one of the first and second phases (i.e. E or R) at least once, and the second well-defined period T represents an interval during which both of the first and second phases E and R are completed at least once. However, as is apparent from Table 1, the relative order of the first and second phases E and R during the second well-defined period T is irrelevant. Thus, T may be defined such that the second phase R precedes the first phase E.

According to the proposed approach, the first amount DMI may be derived based on a first fluid flow parameter FQFI that is registered by the first flow meter Q1. The first flow meter Q1 is arranged on a conduit receiving fresh blood treatment fluid into the apparatus. Thus, the first flow meter Q1 can be arranged downstream (as shown) or upstream of the first fluid pump PF1. Similarly, the second amount DMO may be derived based on a second fluid flow parameter FQFO that is registered by the second flow meter Q2. The second flow meter Q2 is arranged on a conduit discharging used blood treatment fluid from the apparatus. Thus, the second flow meter Q2 can be arranged up-stream (as shown) or downstream of the second fluid pump PF2.

To derive the first amount DMI during the first well-defined interval $T_a$ (or $T_b$ if the second blood flow parameter BQFO is to be determined), the control unit P is preferably configured to apply the following strategy.

(i) At the start of the interval $T_a$, register an initial accumulated mass (or volume) of blood treatment fluid having been fed into the apparatus, $DMI_{start}$, (ii) during the interval $T_a$, update the accumulated mass (or volume) of blood treatment fluid fed into the apparatus based on the first fluid flow parameter FQFI, (iii) at the end of the interval $T_a$, register a final accumulated mass (or volume) of blood treatment fluid having been fed into the apparatus, $DMI_{end}$, and (iv) after the end of the interval $T_a$, calculate $DMI=DMI_{end}-DMI_{start}$.

Analogously, to derive the second amount DMO during the first well-defined interval $T_a$ (or $T_b$ if the second blood flow parameter BQFO is to be determined), the control unit P is preferably configured to apply the following strategy.

(i) At the start of the interval $T_a$, register an initial accumulated mass (or volume) of blood treatment fluid having been discharged from the apparatus, $DMO_{start}$, (ii) during the interval $T_a$, update the accumulated mass (or volume) of blood treatment fluid discharged from the apparatus based on the second fluid flow parameter FQFO, (iii) at the end of the interval $T_a$, register a final accumulated mass (or volume) of blood treatment fluid having been discharged from the apparatus, $DMO_{end}$, and (iv) after the end of the interval $T_a$, calculate $DMO=DMO_{end}-DMO_{start}$.

Finally, the control unit P is preferably configured to determine the first blood flow parameter BQFI (i.e. the average blood flow into the blood treatment unit D during the second well-defined interval $T=T_a+T_b$) as:

$$BQFI = \frac{DMO - DMI}{T} \quad [1]$$

If instead the second blood flow parameter BQFO is to be determined (i.e. the average blood flow out from the blood treatment unit D during the second well-defined interval $T=T_a+T_b$), this parameter may be calculated as:

$$BQFO = \frac{DMI - DMO}{T} \quad [1']$$

According to embodiments of the invention, each of the blood pumps PB1 and PB2 includes a pumping chamber. A flexible member FM1 and FM2 (e.g. in the form of a soft/elastic membrane) separates this pumping chamber into a first accumulation container B1 and B2 respectively, and a second accumulation container F1 and F2 respectively. Each flexible member FM1 and FM2 is movable within its pumping chamber so as to vary a volume relationship between the first and second accumulation containers B1, B2 and F1, F2 respectively. Furthermore, each second accumulation container F1 and F2 is configured to receive an amount of working fluid to act on the flexible member FM1 and FM2 respectively, and thus pump blood through the first accumulation container B1 and B2 respectively. According to the embodiment of the invention shown in FIGS. 1*a* and 1*b*, the fluid pumps PF1 and PF2 respectively and the blood pumps PB1 and PB2 are arranged relative to one another, such that the blood treatment fluid constitutes the working fluid for the blood pumps PB1 and PB2. Hence, the fluid pumps PF1 and PF2 control the operation of the blood pumps PB1 and PB2 via the blood treatment fluid.

The first fluid pump PF1 is configured to draw blood treatment fluid (e.g. dialysis fluid) from the fluid source FS. During the first phase E of the cyclic blood treatment process illustrated in FIG. 1*a*, the first fluid pump PF1 draws a relatively small flow of blood treatment fluid, and pumps this fluid directly into a fluid side of the blood treatment unit D via the first flow meter Q1.

During the first phase of the cyclic blood treatment process, the second fluid pump PF2 is configured to extract/suck fresh blood treatment fluid from the second accumulation container F1 of the first blood pump PB1 and draw this blood treatment fluid through the fluid side of the blood treatment unit D. The operation of the second fluid pump PF2 also causes used blood treatment fluid to be extracted/sucked from the second accumulation container F2 of the second blood pump PB2. After passing the second fluid pump PF2, this blood treatment fluid passes through the second flow meter Q2 and is discharged from the apparatus, e.g. into the drain or the waste compartment FD. The operation of the first and second fluid pumps PF1 and PF2 during the first phase causes a transmembrane flow from the blood side to the fluid side of the blood treatment unit D, or vice versa.

The first blood valve means V1 is configured to control the extraction of untreated blood from the blood source BS via a first needle N1. Analogously, the second blood valve means V2 is configured to control the delivery of treated blood to the target vessel BT via a second needle N2. Of course, in a single-needle implementation the first and second blood valve means V1 and V2 are instead both connected to one needle, which is attached to a patient's blood system.

In any case, during the first (or blood extraction) phase of the cyclic blood treatment process illustrated in FIG. 1*a*, the first blood valve means V1 is open and the second blood valve means V2 is closed. As a result, when the second fluid pump PF2 pulls the fresh blood treatment fluid out from the second accumulation container F1 of the first blood pump PB1, untreated blood is extracted from the blood source BS and fed into the first accumulation container B1 of the first blood pump PB1. Moreover, since the second fluid pump PF2 also draws used blood treatment fluid out from the second accumulation container F2 of the second blood pump PB2, incoming blood continues into the blood side of the blood treatment unit D. Blood located on the blood side of the blood treatment unit D is further pulled into the first accumulation container B2 of the second blood pump PB2. Hence, blood passes through the blood treatment unit D, and as a result, this blood is treated by the blood treatment fluid passing through the fluid side of the blood treatment unit D.

FIG. 1*b* illustrates the second (or blood delivery) phase of the cyclic blood treatment process. In this phase, the first blood valve means V1 is closed while the second blood valve means V2 is open. Preferably, the blood valve means V1 and V2 are controlled via a respective control signal $c_1$ and $c_2$ generated by a control unit P. In contrast to the first phase, during the second phase the first fluid pump PF1 draws a relatively large flow of fresh blood treatment fluid from the fluid source FS. The thus extracted blood treatment fluid continues into the second accumulation container F1 of the first blood pump PB1. The entry of fresh blood treatment fluid into the second accumulation container F1 of the first blood pump PB1, in turn, causes untreated blood located in the first accumulation container B1 of the first blood pump PB1 to be pushed through the blood side of the blood treatment unit D.

Moreover, the operation of the first fluid pump PF1 causes fresh blood treatment fluid to be extracted/sucked from the fluid source FS. After passing through the first flow meter Q1 this blood treatment fluid continues into the fluid side of the blood treatment unit D. Subsequent to passing the blood treatment unit D, the blood treatment fluid continues into the second accumulation container F2 of the second blood pump PB2. This, in turn, causes blood located in the first accumulation container B2 of the second blood pump PB2 to be ejected into the target vessel BT via the second blood valve means V2 and the second needle N2.

Preferably, during the second phase R of the cyclic blood treatment process, the second fluid pump PF2 is also operated to some extent. This causes a fraction of the used blood treatment fluid to exit directly from the blood treatment unit D and be discharged after passing through the second flow meter Q2 (i.e. without being temporarily stored in the second blood pump PB2). The operation of the first and second fluid pumps PF1 and PF2 during the second phase causes a transmembrane flow from blood side to the fluid side of the blood treatment unit D, or vice versa. Thus, by controlling the first and second fluid pumps PF1 and PF2 an amount of fluid drawn from the blood passing through the blood treatment unit D can be adjusted.

Preferably, the control unit P is configured to control the operation of the fluid pumps PF1 and PF2 via first and second motoric signals m1 and m2 respectively.

Moreover, it is advantageous if the control unit P is configured to register pressure parameters (not shown) on the conduit passing the fresh blood treatment fluid into the apparatus, as well as on the conduit discharging used blood treatment fluid from the apparatus. Namely, in response to such pressure measurements, the control unit P may control the valve means V1 and V2 and the fluid pumps PF1 and PF2 such that the apparatus operates according to the cyclic process as outlined above. Specifically, the control unit P may use the above-mentioned pressure parameters to determine appropriate transitions between the first and second phases, and thus control the valve means V1, V2 and the fluid pumps PF1, PF2 as described above. Preferably, the control unit P includes, or is associated with; a memory means M storing computer software for controlling the control unit P to effect the above-described procedure.

However, prior to initiating said cyclic process, so-called priming is normally required. This procedure involves filling and rinsing the apparatus and may be effected as follows. The fluid circuit is filled with fresh blood treatment fluid, such that superfluous fluid rinses the circuit from the fluid source FS. The filling of the fluid causes any air in the dialysis fluid circuit to be pushed back out from the apparatus, e.g. into the waste compartment FD. Correspondingly, the first needle N1 may be connected to a saline solution (or other appropriate fluid) to fill and rinse, and thus eliminate any gas bubbles in the blood circuit.

FIGS. 2*a* and 2*b* show block diagrams over a blood treatment apparatus according to a second embodiment of the invention during the first and second phases E and R respectively of the proposed cyclic treatment process. In FIGS. 2*a* and 2*b* all units and components having reference signs, which also occur in FIGS. 1*a* and 1*b* designate the same units and components as those described above with reference to FIGS. 1*a* and 1*b*.

The second embodiment differs from the first embodiment of the invention in that the blood pumps PB1 and PB2 are not cross-connected relative to the inlet and outlet for receiving fresh blood treatment fluid and discharging used blood treatment fluid respectively. Instead, first and second additional fluid pumps PF3 and PF4 respectively are included to control the blood pumps PB1 and PB2 as desired (i.e. cause the flexible members FM1 and FM2 to reach their respective end positions essentially simultaneously).

The control unit P is configured to control the first additional fluid pump PF3 via a third motoric signal m3, and control the second additional fluid pump PF4 via a fourth motoric signal m4. Specifically, during the first phase E, this involves extracting/sucking used blood treatment fluid from the second accumulation container F1 of the first blood pump PB1 and extracting/sucking fresh blood treatment fluid from the second accumulation container F2 of the second blood pump PB2. During the second phase R, however, the control unit P is configured to operate the first and second additional fluid pumps PF3 and PF4 in the opposite direction, i.e. such that fresh blood treatment fluid is pumped into the second accumulation container F2 of the second blood pump PB2 and used blood treatment fluid is pumped into the second accumulation container F1 of the first blood pump PB1.

FIGS. 3*a* and 3*b* show block diagrams over a blood treatment apparatus according to a third embodiment of the invention during the first and second phases E and R respectively of the proposed cyclic treatment process. In FIGS. 3*a* and 3*b* all units and components having reference signs, which also occur in FIGS. 1*a*, 1*b*, 2*a* and 2*b* designate the same units and components as those described above with reference to FIGS. 1*a*, 1*b*, 2*a* and 2*b*.

The third embodiment differs from the first and second embodiments of the invention primarily in that the blood pumps PB1 and PB2 are controlled via a working fluid, which is separated from the blood treatment fluid. To accomplish this, in the design shown in FIGS. 3*a* and 3*b* the second accumulation container F1 of the first blood pump PB1 is connected to a first working-fluid container W1, and the second accumulation container F2 of the second blood pump PB2 is connected to a second working-fluid container W2. A respective additional fluid pump PF3 and PF4 is arranged on a fluid conduit between each of the working-fluid containers W1 and W2 and the blood pumps PB1 and PB2. Analogous to the embodiment illustrated in FIGS. 2*a* and 2*b*, however, the first and second blood pumps PB1 and PB2 are controlled by the first and second additional fluid pumps PF4 and PF3 respectively. Of course, according to the invention, instead of being separated from one another, the containers W1 and W2 may equally well be represented by a common source of working fluid. Moreover, the working fluid may be any kind of incompressible medium.

In any case, according to this embodiment of the invention, the control unit P is configured to determine the first blood flow parameter BQFI on the further basis of a respective stroke volume $V_{B1}$ and $V_{B2}$ of the blood pumps PB1 and PB2. Namely, in this case, the difference between the first and second amounts of blood treatment fluid DMO and DMI exclusively represents an ultrafiltration parameter between the blood and fluid sides of the blood treatment unit D. Hence, the control unit P is here configured to determine the first blood flow parameter BQFI as:

$$BQFI = \frac{DMO - DMI + V_{B1} + V_{B2}}{T} \qquad [2]$$

where $T = T_a + T_b$.

where DMO and DMI are measured during a first well defined period $T_a$.

FIGS. 4*a* and 4*b* show block diagrams over a blood treatment apparatus according to a fourth embodiment of the invention during the first and second phases E and R respectively of the proposed cyclic treatment process. In FIGS. 4*a* and 4*b* all units and components having reference signs, which also occur in FIGS. 1*a*, 1*b*, 2*a*, 2*b*, 3*a* and 3*b* designate the same units and components as those described above with reference to FIGS. 1*a*, 1*b*, 2*a*, 2*b*, 3*a* and 3*b*.

Similar to the third embodiment, the fourth embodiment differs from the first, second embodiments of the invention in that the blood pumps PB1 and PB2 are controlled by other means than via the blood treatment fluid. However, in contrast to the third embodiment, the design illustrated in FIGS. 4*a* and 4*b* includes blood pumps PB1 and PB2 of piston type. Consequently, the control unit P is configured to: control the first blood pump PB1 via a first piston control signal k1 and control the second blood pump PB2 via a second piston control signal k2.

Piston pumps are advantageous, since by keeping track of the respective piston position, this design renders it possible to determine a pumped volume at arbitrary pump positions, i.e. not only at the end positions. Keeping track of the respective piston pump may be done e.g. by counting steps of a stepping motor driving the piston and thereby determining the accumulated blood volume extracted or returned by the pump. Hence, each stroke volume $V_{B1}$ and $V_{B2}$ of the blood pumps PB1 and PB2 respectively is a variable parameter.

Nevertheless, in further analogy to the third embodiment of the invention, the difference between the first and second amounts of blood treatment fluid DMI and DMO exclusively represents an ultrafiltration parameter between the blood and the fluid sides of the blood treatment unit D, and the first blood flow parameter BQFI is further based on the stroke volumes $V_{B1}$ and $V_{B2}$ of the blood pumps PB1 and PB2 respectively. We can thus use the expression [2] above to determine the first blood flow parameter BQFI.

In order to determine the second blood flow parameter BQFO reflecting the average flow of blood out from the blood treatment unit D, the first and second amounts of blood treatment fluid DMI and DMO are instead determined during the second phase R of the cyclic process. Hence, the first well-defined period of operation is given by $T_b$. Therefore, to determine the second blood flow parameter BQFO, the control unit P is preferably configured to apply strategies as described above under the first and second sets of steps (i)-(iv) with reference to the expression [1], however where the measurements are performed during the interval $T_b$ (as opposed to $T_a$). Analogously, the expression [2] is applicable to the embodiments described in FIGS. 3*a*/3*b* and 4*a*/4*b* for determining second blood flow parameter BQFO.

Generally, in designs where the stroke volumes $V_{B1}$ and $V_{B2}$ of the blood pumps PB1 and PB2 respectively are known, it is possible to determine first and second blood flow parameters $BQFI_a$ respective $BQFO_a$ and $BQFI_b$ respective $BQFO_b$ after each phase E and R respectively of the cyclic process.

Specifically, after completion of the first phase E, the first blood flow parameter $BQFI_a$ may be calculated as:

$$BQFI_a = \frac{DMO - DMI + V_{B2}}{T_a}$$

and the second blood flow parameter $BQFO_a$ may be calculated as:

$$BQFO_a = \frac{V_{B2}}{T_a}.$$

Similarly, after completion of the second phase R, the first blood flow parameter $BQFI_b$ may be calculated as:

$$BQFI_b = \frac{V_{B1}}{T_b}$$

and the second blood flow parameter $BQFO_b$ may be calculated as:

$$BQFO_b = \frac{DMI - DMO + V_{B1}}{T_b}.$$

Additionally, provided that a respective flow measuring means (not shown) is included in the embodiments illustrated in FIGS. 1*a*/1*b*, 2*a*/2*b* or 3*a*/3*b*, which flow meters are configured to register a respective fluid flow QPB1 and QPB2 out from and into, respectively, the first and second blood pumps PB1 and PB2, more specifically out from and into the first and second accumulation containers F1 and F2, it is possible to determine instantaneous blood flow parameters in relation to the blood treatment unit D.

Particularly, during the first phase E, a first instantaneous blood flow parameter $BQFI_{inst-a}$ reflecting the blood flow into the blood treatment unit D in the embodiment shown in FIGS. 1 a and 2*a* may be calculated as:

$$BQFI_{inst-a} = FQFO - FQFI - QPB1$$

For the embodiment shown in FIG. 3*a* it may be calculated as:

$$BQFI_{inst-a} = FQFO - FQFI + QPB2$$

and a second instantaneous blood flow parameter $BQFO_{inst-a}$ reflecting the blood flow out from the blood treatment unit D may be calculated as:

$$BQFO_{inst-a} = QPB2.$$

Furthermore, during the second phase R, the first instantaneous blood flow parameter $BQFI_{inst-b}$ reflecting the blood flow into the blood treatment unit D may be calculated as:

$$BQFI_{inst-b} = QPB1$$

and the second instantaneous blood flow parameter $BQFO_{inst-b}$ reflecting the blood flow out from the blood treatment unit D may for the embodiment shown in FIGS. 1*b* and 2*b* be calculated as:

$$BQFO_{inst-b} = FQFI - FQFO - QPB2$$

For the embodiment shown in FIG. 3*b* it may be calculated as:

$$BQFO_{inst-b} = FQFI - FQFO + QPB1$$

In an alternative embodiment of the arrangements shown in FIGS. 1*a*, 1*b*, 2*a*, 2*b*, 3*a* and 3*b* the flow measuring means described above, possibly in cooperation with the control unit P, are configured to accumulate a mass (or volume) of treatment fluid or working fluid fed into, or discharged from, the respective second accumulation container F1, F2. This design renders it possible to determine a pumped mass (or volume) at arbitrary positions of the respective flexible member FM1, FM2, i.e. not only at the end positions. Hence, the stroke volume $V_{B1}$ and $V_{B2}$ of the blood pumps PB1 and PB2 is a variable parameter and thus selectable in the same way as described in connection with the piston pumps disclosed in FIG. 4*a*, 4*b*. Consequently, the control unit P is configured to control the first and the second blood pump PB1; PB2 respectively via the relevant motoric control signals m1, m2, m3 and m4 such that when a certain accumulated volume is reached, the relevant control signal controls the relevant fluid pumps PF1, PF2; PF3, PF4 to pass working fluid in a reversed direction with respect to the second accumulation containers F1, F2 to effect a transition between e.g. the first and the second phase of operation E and R respectively. The ability to select the stroke volume is advantageous e.g. for small patients, where a too large stroke volume in some cases may cause disturbances in the cardiovascular system, either short term or long term. On the other hand a large stroke volume enables a higher average blood flow rate through the blood treatment unit, and thus may improve the efficiency of the treatment of the blood.

An alternative embodiment of the blood treatment apparatus, initially described, comprises a control unit P and a measuring means configured to emit a feedback signal indicative of the amount of working fluid received into, or discharged from at least one of the second accumulation containers F1, F2 whereby the pumped volume of working fluid is determined by the control unit P at an arbitrary position of the flexible member FM1, FM2.

The measuring means may be configured to register a working fluid flow QPB1, QPB2 or a time with a constant fluid flow QPB1, QPB2 and the control unit P may be configured to determine an accumulated amount of working fluid received into, or discharged from at least one of the second accumulation containers F1, F2.

The flow measuring means may e.g. be constituted by a device comprising a piston pump with a controlled infusion of fluid, a device comprising a pair of scales or a device comprising a means for flow restriction and a means for measuring pressure drop over the means for flow restriction.

As described above the control unit P may be configured to register a pressure parameter related to the working fluid received into, or discharged from at least one of the second accumulation containers F1, F2. In one embodiment this pressure parameter is used to determine an end position of the flexible member FM1, FM2. The end position may be utilized to determine an initial start volume equal to zero when changing between phases E, R and starting to accumulate a mass or volume of working fluid pumped into or discharged from at least on of the second accumulation containers F1, F2.

To sum up, we will now describe the proposed blood-flow-measurement method with reference to the flow diagram in FIG. 5. Here, we presume that the blood treatment apparatus includes: a blood treatment unit configured to receive untreated blood and fresh blood treatment fluid, and emit treated blood and used blood treatment fluid. A pair of fluid pumps is configured to pass blood treatment fluid through the blood treatment unit and a pair of blood pumps is configured to extract untreated blood from a blood source, pass extracted blood through the blood treatment unit and deliver treated blood to a target vessel. For reasons of clarity, we also presume that the first well-defined period is represented by $T_a$ (i.e. that $T_b$ is subsequent to $T_a$ within T). However, of course, the first well-defined period may equally well be represented by $T_b$. As discussed above, in such a case the first and second well-defined periods instead end simultaneously.

A first step 510 checks whether or not a start criterion has been fulfilled, and if not, the procedure loops back and stays in step 510. If the start criterion is found to be fulfilled, a step 520 follows. Technically, the start criterion may correspond to any type of event. However, preferably the start criterion is deemed fulfilled in connection with transitioning between the above-mentioned first and second phases of operation E and R respectively. Such a transition, in turn, may be detected via various pressure measurements, and/or in response to closing or opening one or more of the first and second blood valve means V1 and V2. Alternatively such a transition may be initiated arbitrarily by means of volume measurements or fluid measurements as described above.

Step 520 starts time measurement to determine the duration of the second well-defined period of operation of the apparatus. Thereafter, a step 530 registers a first amount of fresh blood treatment fluid received into the apparatus comprising the blood treatment unit. Preferably, this is effected accumulatively as out-lined above with reference to the first set of steps (i)-(iv) and the expression [1]. In parallel with step 530, a step 540 registers a second amount of used blood treatment fluid emitted from the apparatus. Preferably, this also is effected accumulatively as outlined above with reference to the second set of steps (i)-(iv) and the expression [1].

After each updating of the accumulated first and second amounts in steps 530 and 540, a step 550 checks whether or not an end criterion for the first well-defined period is fulfilled, and if so, a step 560 follows. Otherwise, the procedure loops back to steps 530 and 540 for continued updating of the first and second amounts. Step 560 checks whether or not an end criterion for the second well-defined period is fulfilled, and if so, a step 570 follows. Otherwise, the procedure loops back and stays in step 560.

Step 570 stops the time measurement initiated in step 520, i.e. defines the extension of the second well-defined period of operation of the apparatus. Subsequently, a step 580 determines the blood flow parameter based on a difference between the first and second amounts and the duration of the second well-defined period. The blood flow parameter thus expresses an average blood flow in relation to the blood treatment unit during the second well-defined period.

Thereafter, the procedure loops back to step 510, and preferably, the procedure iterates as described above until the treatment is finalized.

All of the steps, as well as any sub-sequence of steps, described with reference to FIG. 5, above may be controlled by means of a programmed computer apparatus. Moreover, although the embodiments of the invention described above with reference to the drawings comprise computer apparatus and processes performed in computer apparatus, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the procedure according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc), an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant procedures.

In an alternative flow measurement method the following steps are comprised; registering the amount of the working fluid received into, or discharged from at least one of the second accumulation containers F1, F2 of at least one of the blood pumps PB1, PB2, emitting a feedback signal being indicative of the accumulated amount of working fluid received in the second accumulation container F1, F2, based on the feedback signal, determining the pumped volume at an arbitrary position of the flexible member FM1, FM2, at a certain volume reversing the direction of the working fluid with respect to the second accumulation container F1;F2 and thereby effecting the arbitrary transition between e.g. a first and a second phase E, R.

The amount of working fluid may be registered by a means for measuring of the working fluid flow QPB1, QPB2. Alternatively the amount of working fluid may be registered by a means for measuring a time durance of a constant flow of working fluid QPB1, QPB2.

One embodiment of the method comprises pumping the treatment fluid by means of the fluid pumps PF1, PF2 and controlling operation of the blood pumps PB1, PB2 via the pumped blood treatment fluid. An alternative embodiment of the method comprises controlling the blood pumps PB1, PB2 via a working fluid which is fluidly separated from the blood treatment fluid. However, also in this embodiment the working fluid as such may be constituted by the blood treatment fluid.

In an alternative embodiment of the method one phase shift, e.g. transition between the return phase, R, and extraction phase, E, is effectuated at an end position of the flexible member FM1, FM2 and the transition between the extraction phase, E, and the return phase, R, is effectuated at an arbitrary position of the flexible membrane FM1, FM2. The end position of the membrane may be determined by the control unit, P, based on registered pressure parameters as described above.

In this specification, the wording that: "a fluid pump is arranged in a conduit" shall be understood to also encompass arrangements wherein the pump is configured to operate on a fluid passing through the conduit by other means than having the pump actually included in the conduit, such as hose pumps manipulating the exterior of a fluid conduit.

The reference to any prior art in this specification is not, and should not be taken as, an acknowledgement or any suggestion that the referenced prior art forms part of the common general knowledge in Australia, or in any other country.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A blood treatment apparatus, comprising:

a blood treatment unit configured to receive untreated blood and fresh blood treatment fluid, and emit treated blood and used blood treatment fluid, a pair of fluid pumps configured to pass the blood treatment fluid through the blood treatment unit, a pair of blood pumps configured to extract untreated blood from a blood source, pass extracted blood through the blood treatment unit and deliver treated blood to a target vessel, and a flow measurement device configured to determine at least one blood flow parameter reflecting a flow of blood in relation to the blood treatment unit, wherein the flow measurement device is configured to determine the at least one blood flow parameter based on a difference between:

a first amount of the fresh blood treatment fluid received into the apparatus, and a second amount of the used blood treatment fluid emitted from the apparatus, the first and second amounts being registered during a first period of operation of the apparatus, and the at least one blood flow parameter representing an average blood flow during a second period.

2. The blood treatment apparatus according to claim 1, wherein the apparatus is configured to operate according to a cyclic process of which during a first phase the untreated blood is extracted from the blood source, and during a second phase the treated blood is delivered to the target vessel, the first period representing the time required to complete one of the first and second phases at least once, and the second period representing an interval during which both of the first and second phases are completed at least once.

3. The blood treatment apparatus according to claim 2, wherein the fluid pumps are configured to control the operation of the blood pumps via the blood treatment fluid.

4. The blood treatment apparatus according to claim 3 comprising a control unit and a flow measuring means configured to register a working fluid flow received into, or discharged from at least one of the second accumulation containers and emit a feedback signal to the control unit the feedback signal being indicative of the accumulated amount of working fluid whereby the pumped mass or volume is determined by the control unit at an arbitrary position of the flexible member.

5. The blood treatment apparatus according to claim 2, further comprising a controller controlling the blood pumps via a working fluid separated from the blood treatment fluid, and the flow measurement device is configured to determine the blood flow parameter based on a respective stroke volume of the blood pumps.

6. The blood treatment apparatus according to claim 2, wherein at least one of the blood pumps is of piston type, and the apparatus comprises mechanical controller controlling the at least one piston-type blood pump in direct response to a respective control signal , and the control unit is configured to determine the blood flow parameter based on a respective stroke volume of the blood pumps.

7. The blood treatment apparatus according to claim 2, wherein a first parameter of the at least one blood flow parameter reflects a flow of blood into the blood treatment unit, the first period of operation represents a duration of the first phase, and the second d period represents the duration of the first phase plus the duration of one second phase temporally adjoining the first phase.

8. The blood treatment apparatus according to claim 2, wherein a second parameter of the at least one blood flow parameter reflects a flow of blood out from the blood treatment unit, and the first period of operation represents a duration of the second phase, and the second period represents the duration of the second phase plus the duration of one first phase temporally adjoining the second phase.

9. The blood treatment apparatus according to claim 1, wherein the blood treatment unit comprises a semi-permeable membrane structure, the blood is being passed on a blood side of said structure, and the blood treatment fluid is being passed on a fluid side of said structure, and the apparatus includes an ultrafiltration device determining an ultrafiltration parameter between the blood and the fluid sides based on a difference between the first and second amounts.

10. An extracorporeal blood circuit comprising:

a blood treatment unit including a blood input to receive untreated blood, an fluid input to receive a fresh blood treatment fluid, a blood output to discharge treated blood and a fluid output to discharge an effluent fluid from the blood treatment unit;

a first fluid pump moving the blood treatment fluid to the fluid input and a second fluid pump moving the effluent fluid from the fluid output;

a first blood pump moving the untreated blood to the blood input of the blood treatment unit and a second blood pump moving the treated blood from the blood output, and a control unit executing a computer program stored on a non-transitory storage medium, wherein the computer program causes the control unit to:

calculate a difference between a first amount of the fresh blood treatment fluid received by the blood treatment unit during a first period and a second amount of the used blood treatment fluid discharged from the blood treatment unit during the first period, and determine an average blood flow during a second period based on the calculated difference.

11. The extracorporeal blood circuit according to claim 10, wherein the circuit further comprises a first operational phase during which the untreated blood is extracted from the blood source, a second operational phase during which the treated blood is delivered to the target vessel, wherein the first and second operational phases occur successively and cyclically, and the first period represents a period for completing one of the first and second phases at least once, and the second period represents an interval during which both of the first and second phases are completed at least once.

12. The extracorporeal blood circuit according to claim 10, wherein the first and second fluid pumps are configured to control the operation of the blood pumps via the blood treatment fluid.

13. The extracorporeal blood circuit according to claim 10, wherein the first and second blood pumps are actuated by a working fluid separated from the blood treatment fluid.

14. The extracorporeal blood circuit according to claim 10, wherein at least one of the first and second blood pumps is a piston type blood pump.

15. The extracorporeal blood circuit according to claim 10, wherein:

the blood treatment unit comprises a semi-permeable membrane structure, the blood is being passed on a blood side of said structure, and the blood treatment fluid is being passed on a fluid side of said structure.

* * * * *

UNITED STATES PATENT AND TRADEMARK OFFICE

CERTIFICATE OF CORRECTION

PATENT NO. : 8,485,999 B2
APPLICATION NO. : 13/124258
DATED : July 16, 2013
INVENTOR(S) : Holmer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 201 days.

Signed and Sealed this
Eighth Day of September, 2015

Michelle K. Lee
*Director of the United States Patent and Trademark Office*